United States Patent [19]
Bethell et al.

[11] Patent Number: 5,852,205
[45] Date of Patent: Dec. 22, 1998

[54] CATALYTIC PROCESS

[75] Inventors: Donald Bethell, Wirral; Graham John Hutchings, Osmotherley; Christopher Langham, Newark; Philip Charles Bulman Page, Loughborough; Darren Frank Lee, West Derby, all of United Kingdom

[73] Assignee: Imperial Chemical Industries PLC, United Kingdom

[21] Appl. No.: 935,331

[22] Filed: Sep. 22, 1997

[30] Foreign Application Priority Data

Sep. 20, 1996 [GB] United Kingdom ................... 9719725

[51] Int. Cl.$^6$ .................................................. C07D 203/06
[52] U.S. Cl. ........................... 548/965; 548/967; 548/969
[58] Field of Search ..................... 548/969, 965, 548/967

[56] References Cited

FOREIGN PATENT DOCUMENTS

| | | |
|---|---|---|
| 44 09 310 A1 | 3/1994 | Germany . |
| 04 187 514 | 6/1992 | Japan . |
| WO 89/06229 | 7/1989 | WIPO . |

OTHER PUBLICATIONS

Corma et al., J. Am. Chem. Soc. 1994, 116 No. 6, pp. 2276–2280.
Evans et al., J. Am. Chem. Soc., 1993, 115 No. 12, pp. 5328–5329.
Evans et al., J. Am. Chem. Soc., 1994, 116 No. 7, pp. 2742–2753.
Feast et al., Studies in Surface Science and Catalysis, (11th International Congress on Catalysis Anniversary 101 Part A (1966) pp. 211–219.
Mohan et al., Chemical Communiations, 1997, No. 15, pp. 1429–1430.
Muller et al., Journal of Physical Organic Chemistry, vol. 9, 1996, pp. 341–347.
Sodergren et al., Tetrahedron Letters, vol. 38, No. 39, 1997, pp. 6897–6900.
CA:114 100883 On the mechanism . . . compounds. Atgai et al., 1991.
CA: 111:Functionalization of olefins by alkoxyimidoylnitrenes. Subbaraj et al., 1989.

*Primary Examiner*—Joseph K. McKane

[57] ABSTRACT

Production of aziridines comprising reacting an ethylenically unsaturated compound, such as styrene or methyl cinnamate, with a nitrene donor, such as (N-(p-tolylsulphonyl) imino) phenyliodinane in the presence of an acidic zeolitic material having a pore size large enough for the reactants to enter, and the aziridination product to leave, the zeolite supercage, said zeolite having been impregnated, or preferably exchanged, with ions of at least one metal selected from Groups VIA, VIIA, VIII, IB and IIB of the 4th to the 6th periods of the Periodic Table. The metal is preferably copper and the zeolite is preferably zeolite Y.

Asymmetric aziridines may be made by treating the catalyst with a chiral modifier such as a 4,4'-disubstituted bis(oxazoline) before contact with the nitrene donor.

10 Claims, No Drawings

CATALYTIC PROCESS

Catalytic Process

This invention relates to a catalytic process and in particular to the heterogeneous catalysis of the aziridination of ethylenically unsaturated compounds. Such aziridines are useful chemical intermediates or reagents for use in the production of fine chemicals such as pharmaceuticals.

The aziridination of ethylenically unsaturated compounds involves the reaction of the ethylenically unsaturated compound with a nitrene donor compound. As is described by Evans et al in J. Am. Chem. Soc. (1993), 115, pages 5328–5329 and J. Am. Chem. Soc. (1994), 116, pages 2742–2753, aziridination of ethylenically unsaturated compounds may be effected by homogeneous catalysis using copper salts such as copper trifluoroacetate as catalysts and (N-(p-tolylsulphonyl) imino) phenyliodinane (hereinafter PhI=NTs) as the nitrene donor. To enable the product to be more readily separated from the reaction mixture, it would be desirable to employ a heterogeneous catalyst. We have found suitable heterogeneous catalysts.

Accordingly the present invention provides a process for the production of aziridines comprising reacting an ethylenically unsaturated compound with a nitrene donor in the presence of an acidic zeolitic material having a pore size large enough for the reactants to enter, and the aziridination product to leave, the zeolite supercage, said zeolite having been impregnated, or preferably exchanged, with ions of at least one metal selected from Groups VIA, VIIA, VIII, IB and IIB of the 4th to the 6th periods of the Periodic Table (as set out in the UK Abridgements of Patent Specifications for the Series 1525001 to 1537580). Such metals are Cr, Mn, Fe, Co, Ni, Cu, Zn, Mo, Tc, Ru, Rh, Pd, Ag, Cd, W, Re, Os, Ir, Pt, Au, and Hg. Preferred metals are Mn, Fe, Ni, Cu, Ru, Rh, Ag, Ir, and Hg. Copper is most preferred.

The zeolite employed will depend on the nature of the reactants and the aziridination product. In most cases zeolite Y can be used, but a larger pore size zeolite may be desirable in other cases. For example, using PhI=NTs as the nitrene donor, aziridination of methyl cinnamate (methyl trans-3-phenylpropenoate) can be effected using copper exchanged zeolite Y, but a larger pore zeolite is required for aziridination of stilbene (trans-1,2 diphenyl ethylene). The unexchanged zeolite should have some acidity and so preferably contains at least some alumina. Thus larger pore size zeolites such as the silicalite MCM can be employed if a small proportion of an alumina source is incorporated into the zeolite preparation to form Bronsted acid sites. For most reactants, a copper exchanged zeolite Y is preferred.

We have found that the catalyst should not contain substantially more than about 2 atoms of the aforesaid metal per zeolite supercage. Thus for copper exchanged zeolite Y, the exchanged catalyst preferably contains 0.1 to 7% by weight of copper.

The catalyst may be made by calcining an ammonium form of the zeolite as prepared so as to form the H version. This is then slurried in an aqueous solution of a salt of the desired metal, and the slurry stirred for e.g. 24 hours at room temperature. The exchanged zeolite is then separated by filtration or by centrifuging, washed to remove any unbound metal ions, and dried. Before use the exchanged zeolite should be calcined to remove any remaining or adsorbed water.

The ethylenically unsaturated compound may be an olefin such as ethylene, propylene, butene, pentene, hexene or cyclohexene, or may be an aromatic ethylenically unsaturated compound, such as styrene or a substituted styrene such as α-methyl styrene, p-chloro styrene or p-methyl styrene, stilbene (trans-1,2 diphenyl ethylene), or methyl cinnamate (methyl trans-3-phenylpropenoate).

PhI=NTs is the preferred nitrene donor, although other nitrene donors such as 3-acetoxyaminoquinazolines, trialkylammonium imides ortoluene sulphonyl azide may be used.

The reaction may be carried out in the presence of a suitable solvent for the reactants: examples of solvents include toluene, benzene, dichloromethane, and acetonitrile. Acetonitrile is the preferred solvent. Alternatively provided that the nitrene donor and the aziridination product are soluble in the ethylenically unsaturated compound, the reaction may be carried out in the absence of a solvent.

The reaction temperature employed may depend upon the nature of the solvent (if any) and the nitrene donor but is preferably in the range −40° C. to +60° C. For PhI=NTs as the nitrene donor, the reaction is preferably effected at a temperature in the range −25° C. to +35° C.

The reaction may be effected at any suitable pressure, e.g. atmospheric, although where the ethylenically unsaturated compound is volatile or gaseous at the reaction temperature, the reaction pressure should be sufficient to maintain the ethylenically compound in the liquid state e.g. in solution.

The process may be effected in the presence of an excess of one of the reactants, e.g. the ethylenically unsaturated compound. However while it is desirable when using a homogeneous catalyst to employ a substantial excess of the ethylenically unsaturated compound, e.g. about 5 or more moles of the ethylenically unsaturated compound per mole of nitrene donor, such a large excess is not necessary with the catalysts employed in the present invention, and indeed equimolar amounts of the ethylenically unsaturated compound and nitrene donor may be employed.

The process may be effected batchwise or continuously. In a batch reaction, to obtain a useful reaction rate, the amount of catalyst employed is preferably such that there are about 0.1 to 0.5, preferably 0.2 to 0.3, gram atoms of the catalytic metal per mole of nitrene donor.

A typical batch reaction procedure involves forming a solution of the ethylenically unsaturated compound in the solvent, adding the catalyst containing the metal ions, adding the nitrene donor, and stirring until the nitrene donor has reacted. The solution of the aziridination product can then be separated from the catalyst by filtration or centrifuging.

Enantioselective aziridination may be effected by homogeneous catalysis (see the aforementioned J. Am. Chem. Soc. (1993), 115, 5328–5329 reference) by including a chiral modifier such as a 4,4'-disubstituted bis(oxazoline) into the reaction mixture. Surprisingly such enantioselective aziridination may also be effected in the present invention. In the present invention the catalyst is treated with the chiral modifier before contact with the nitrene donor. However, we have found that the amount of chiral modifier required is considerable less than with homogeneous catalysis. Thus whereas it is usual in homogeneous catalysis to use one or more moles of chiral modifier per gram atom of the catalytic metal, in the present invention if more than one mole of chiral modifier is used per gram atom of catalytic metal, the yields of aziridine are decreased, possibly as a result of the excess of chiral modifier blocking the zeolite supercage. We prefer to employ not more than one mole of chiral modifier per gram atom of the catalytic metal. In contrast to the findings reported by Evans et al in the aforesaid J. Am. Chem. Soc. (1993), 115, pages 5328–5329 for homogeneous catalysis, when using a chiral modifier it is preferred to employ a polar solvent, such as acetonitrile.

When employing a chiral modifier to give asymmetric aziridination, it is desirable to operate at lower temperatures, within the aforementioned temperature range, than when operating in the absence of a chiral modifier so that the enantiomer excess can be increased. However, operation at too low a temperature results in decreased yields. Preferably the temperature is in the range −20° C. to −10° C.

In a typical procedure for enantioselective aziridination, the exchanged zeolite is added to the solvent and the chiral modifier is then added. The slurry is stirred for sufficient time, e.g. 15 min., for the chiral modifier to complex with the catalytic metal and then the ethylenically unsaturated compound and the nitrene donor are added.

The invention is illustrated by the following examples.

EXAMPLE 1

Preparation of Catalyst

The ammonium form of zeolite Y was calcined in air at 550° C. for 10 hours to form the H form of the zeolite. 10 g of the H zeolite was slurried in 200 ml of aqueous 0.5 molar copper acetate solution and stirred at room temperature for 24 hours. The exchanged zeolite was separated by centrifuging, washed, and dried at 110° C. Before use in the following aziridination reactions, the exchanged zeolite was calcined in air at 550° C. for 10 hours. The catalyst contained about 5% by weight of copper.

EXAMPLES 2–10

Aziridination of Methyl Cinnamate 0.36 g of methyl cinnamate was added to 5 ml of acetonitrile. 0.145 g of the catalyst powder as prepared in Example 1 was added, and then 0.167 g of PhI=NTs was added. [The proportions are such that there was 5 moles of methyl cinnamate per mole of PhI=NTs and 0.25 gram atoms of copper per mole of PhI=NTs.] The slurry was stirred at 25° C. for 24 hours and then the solution filtered from the catalyst. The solution was then analysed chromatographically.

The above procedure was repeated using other ethylenically unsaturated compounds in place of methyl cinnamate. The proportions of ingredients, reaction conditions, and yields were as shown in the following table.

The reduced yield of Example 5 compared to Example 3 was thought to be the result of the decreased amount of catalyst giving a slower reaction and hence an increased proportion of the PhI=NTs decomposed to toluene sulphonamide and iodobenzene.

By way of comparison, example 2 was repeated using trans-stilbene in place of methyl cinnamate. No aziridine was formed. Molecular modelling showed that although methyl cinnamate is of similar size to trans-stilbene, whereas the N-tosylaziridine formed from methyl cinnamate can easily fit through the pores of zeolite Y, the N-tosylaziridine formed from trans-stilbene is too bulky to diffuse through the connecting channels within the zeolite.

EXAMPLE 11

A sample of the dried copper-exchanged catalyst was resuspended in a fresh amount of the copper acetate solution and the slurry stirred for 24 hours at room temperature. The solid was separated by centrifuging, washed dried and calcined as in Example 1. The resultant catalyst contained 7% by weight copper.

Another catalyst was made by the procedure of Example 1 but using 0.2 molar copper acetate solution to give a product containing 3% by weight copper.

These catalysts were used for the aziridination of styrene by the procedure of Example 3, using such an amount of catalyst that there was 0.25 moles of copper per mole of PhI=NTs in each case. The catalysts containing 3% and 5% by weight of copper gave similar reaction rates and yields whereas that containing 7% by weight copper gave no aziridine. It is thought that this catalyst contained such an amount of copper within the zeolite pores that there was insufficient room in the supercage for the reactants and/or aziridination product.

EXAMPLES 12–24

Asymmetric Aziridination of Styrene

Example 3 was repeated except that the catalyst of Example 1 was suspended in 5 ml of solvent at the desired reaction temperature and a chiral modifier, 4,4'-diphenyl bis(oxazoline), was added and the mixture stirred for 15 minutes before adding the styrene and PhI=NTs. The amount of chiral modifier, solvent, reaction temperature, yield and enantiomer excess are shown in the following table. The enantiomer excess is defined as the difference between the amounts of the enantiomers divided by the sum of the amounts of the enantiomers, i.e. (R−S)/(R+S).

| Example | ethylenically unsaturated compound | moles per mole of PhI = NTs | g atoms of copper per mole of PhI = NTs | yield of aziridine (moles per 100 moles of PhI = NTs) |
| --- | --- | --- | --- | --- |
| 2 | methyl cinnamate | 5 | 0.25 | 84 |
| 3 | styrene | 5 | 0.25 | 90 |
| 4 | styrene | 1 | 0.25 | 87 |
| 5 | styrene | 5 | 0.05 | 62 |
| 6 | α-methyl styrene | 5 | 0.25 | 33 |
| 7 | p-chloro styrene | 5 | 0.25 | 76 |
| 8 | p-methyl styrene | 5 | 0.25 | 66 |
| 9 | cyclohexene | 5 | 0.25 | 50 |
| 10 | trans-2-hexene | 5 | 0.25 | 44 |

| Example | solvent | chiral modifier (moles per mole of PhI = NTs) | Temp (°C.) | yield (moles per 100 moles of PhI = NTs) | enantiomer excess (%) |
|---|---|---|---|---|---|
| 12 | acetonitrile | 0.5 | −20 | 17 | 30 |
| 13 | acetonitrile | 0.2 | −20 | 46 | 36 |
| 14 | acetonitrile | 0.2 | −20 | 80 | 34 |
| 15 | acetonitrile | 0.1 | −20 | 50 | 36 |
| 16 | acetonitrile | 0.05 | −20 | 86 | 35 |
| 17 | acetonitrile | 0.025 | −20 | 77 | 36 |
| 18 | acetonitrile | 0.05 | −35 | 22 | 32 |
| 19 | acetonitrile | 0.05 | −10 | 76 | 43 |
| 20 | acetonitrile | 0.05 | 0 | 72 | 26 |
| 21 | acetonitrile | 0.05 | +25 | 80 | 18 |
| 22 | dichloromethane | 0.05 | −20 | 5 | 19 |
| 23 | toluene | 0.05 | −20 | 2 | 13 |
| 24 | benzene | 0.05 | −20 | 32 | 12 |

In Example 14, after stirring the catalyst with the oxazoline, the catalyst was filtered off, washed with acetonitrile and then used as the catalyst in a fresh amount of solvent. The results are similar to those obtained in Example 16. It is noted that in the other examples where more than 0.05 moles of oxazoline per mole of PhI=NTs was employed, i.e. Examples 12, 13 and 15, the yield was decreased compared to that of Examples 14 and 16. This is suggestive that in the Examples 12, 13, and 15 some of the oxazoline is superfluous and is hindering the free passage of the reactants and/or aziridine through the zeolite pores.

Examples 16 and 18 to 21 indicate that operation in the temperature range −20° C. to −10° C. is advantageous where asymmetric aziridination is desired.

Examples 16 and 22 to 24 indicate that operation in a polar solvent such as acetonitrile is desirable in order to obtain high yields and acceptable enantiomeric excesses.

EXAMPLE 25

Example 19 was repeated using 2,6-bis [(4S)-isopropyl-2-oxazolin-2-yl] pyridine as the chiral modifier in place of 4,4'-diphenyl bis(oxazoline). The yield was 4 moles per 100 moles of PhI=NTs and the enantiomer excess was 61%.

EXAMPLE 26

The procedure of Example 16 was repeated using methyl cinnamate in place of styrene. The yield was 8 moles per 100 moles of PhI=NTs and the enantiomer excess was 61%. In contrast to the homogeneous catalysis reported by Evans et al in the aforesaid J. Am. Chem. Soc. (1993), 115, pages 5328–5329, where use of benzene as the solvent gave an increased yield and enantiomer excess compared to acetonitrile as the solvent, when this experiment was repeated using benzene as the solvent, the yield was only 1 mole per 100 moles of PhI=NTs and the enantiomer excess was only 34%.

We claim:

1. A process for the production of aziridines by heterogeneous catalysis comprising reacting an ethylenically unsaturated compound with a nitrene donor in the presence of an acidic zeolitic material impregnated, or exchanged, with ions of at least one metal selected from Groups VIA, VIIA, VIII, IB and IIB of the 4th to the 6th periods of the Periodic Table and having a pore size large enough for the reactants to enter and the aziridination product to leave, a zeolite supercage.

2. A process according to claim 1 wherein the metal is copper.

3. A process according to claim 1 wherein the zeolite is zeolite Y.

4. A process according to claim 1 wherein the catalyst is a metal exchanged acidic zeolite containing not more than 2 of said metal atoms per zeolite supercage.

5. A process according to claim 1 wherein the catalyst contains 0.1 to 7% by weight of the metal.

6. A process according to claim 1 wherein the nitrene donor is (N-(p-tolylsulphonyl) imino) phenyliodinane.

7. A process according to claim 1 wherein the reaction is effected at a temperature in the range −40° C. to +60° C.

8. A process according to claim 1 wherein the catalyst is treated with a chiral modifier before contacting with the nitrene donor.

9. A process according to claim 8 wherein the reaction of the nitrene donor and the ethylenically unsaturated compound is effected at a temperature in the range −20° C. to −10° C.

10. A process according to claim 1 wherein the reaction is effected in the presence of a polar solvent.

* * * * *